(12) United States Patent
Palzer et al.

(10) Patent No.: US 8,790,728 B2
(45) Date of Patent: Jul. 29, 2014

(54) NATURAL TASTE ENHANCING SAVOURY BASE AND A PROCESS FOR ITS PREPARATION

(75) Inventors: Stephan Palzer, York (GB); David Nikolic, Bergheim (DE); Pieter Berends, Zoznegg-Muhlingen (DE); Dac Thang Ho, Le Mont-sur-lausanne (CH); Yvette Fleury Rey, Ursy (CH); Helge Ulmer, Bad Windsheim (DE); Silke Schopp, Singen (DE); Daniel Sebastian Appel, Beuren an der Aach (DE); Thomas Raab, Grandvaux (CH)

(73) Assignee: Nestec S.A., Vevey (CH)

( * ) Notice: Subject to any disclaimer, the term of this patent is extended or adjusted under 35 U.S.C. 154(b) by 49 days.

(21) Appl. No.: 13/256,849

(22) PCT Filed: Mar. 23, 2010

(86) PCT No.: PCT/EP2010/053735
§ 371 (c)(1),
(2), (4) Date: Nov. 16, 2011

(87) PCT Pub. No.: WO2010/108901
PCT Pub. Date: Sep. 30, 2010

(65) Prior Publication Data
US 2012/0315354 A1    Dec. 13, 2012

(30) Foreign Application Priority Data
Mar. 25, 2009 (EP) ........................ PCT/EP09/053530

(51) Int. Cl.
A23L 1/23       (2006.01)
A23L 1/229      (2006.01)

(52) U.S. Cl.
USPC .............. 426/7; 426/650; 426/590; 426/589

(58) Field of Classification Search
CPC ................................ A23L 1/23; A23L 1/229

USPC ...................................... 426/7, 650, 590, 589
See application file for complete search history.

(56) References Cited

U.S. PATENT DOCUMENTS 6,838,100 B2      1/2005   Jaeger et al.
2007/0269871 A1*  11/2007  Zelder et al. ................. 435/113

FOREIGN PATENT DOCUMENTS

EP    2042043    4/2009
GB    1107693    3/1968

OTHER PUBLICATIONS

Tomita K et al: "Stimulation by L Proline of 5' Inosinic Acid Production by Mutants of *Corynebacterium-ammoniagenes*" Agricultural and Biological Chemistry, vol. 55, No. 9, (1991) pp. 2221-2226, XP002234343.
PCT International Search Report for International Application No. PCT/EP2010053735 with a Mailing Date of Dec. 5, 2010, 4 pages.
Written Opinion of the PCT International Searching Authority for International Application No. PCT/EP2010053735 with a Mailing Date of Dec. 5, 2010, 13 pages.

* cited by examiner

*Primary Examiner* — D. Lawrence Tarazano
*Assistant Examiner* — Hamid R Badr
(74) *Attorney, Agent, or Firm* — K&L Gates LLP

(57) ABSTRACT

A taste enhancing savoury base comprises between 8 to 80% of naturally derived compounds taken in the group consisting of glutamate, IMP and GMP, and further comprises naturally food derived compounds such as organic acids and their salts, amino acids, peptides and aroma compounds. The base is obtained through a prokaryotic fermentation with a bacteria taken from the group consisting of *Corynebacterium glutamicum, Corynebacterium ammoniagenes, Corynebacterium casei, Corynebacterium efficiens, Brevibacterium lactofermentum* and *Bacillus subtilis*. The base is not purified by crystallization or chromatographic methods.

9 Claims, No Drawings

NATURAL TASTE ENHANCING SAVOURY BASE AND A PROCESS FOR ITS PREPARATION

CROSS REFERENCE TO RELATED APPLICATIONS

The present application is a National Stage of International Application No. PCT/EP2010/053735, filed on Mar. 23, 2010, which claims priority to International Application No. PCT/EP2009/053530 (EP), filed on Mar. 25, 2009, the entire contents of which are being incorporated herein by reference.

The present invention concerns a natural shelf-stable taste enhancing savoury base and a process for its preparation.

The GB Patent 1107693 concerns already a process for the preparation of seasonings or flavourings from microorganisms. This invention relates to a process wherein either the broth is discarded or wherein the process is non natural. According to examples 1, 2, 5, 6 and 7 of this patent, they discard the liquid broth and work on the cell pellets. According to examples 3 and 4 of this patent, they do not process on natural way, but with use of chemicals, the cells and liquid broth are processed further, the glutamic acid (main fermentation product) is substantially removed and a treatment with NaOH, sodium bicarbonate, HCl and enzymes and adsorbtive resins is carried out. The U.S. Pat. No. 6,838,100 concerns a process for the preparation of a cultured savoury base, which comprises hydrolyzing for a sufficient time to prepare a savoury material, a protein containing material using a combination of at least one enzyme with at least one thermotolerant lactic acid bacteria strain selected for its ability to provide a glutaminase activity (such that the base maintains glutaminase activity) in order to provide glutamic acid or a glutamate in the base in an amount sufficient to enhance body and taste. The umami taste obtained by following this way of procedure is not high enough. Therefore, it is necessary to add to these preparations purified MSG (Mono-Sodium-Glutamate) and nucleotides (IMP: Inosine Monophosphate and GMP: guanosine Monophosphate), or yeast extracts. The problem with such a procedure is that it is not natural or in the presence of yeast extract gives a yeasty taste to the final product.

It is therefore an object of the present invention to provide a natural food composition that is useful to provide easily and conveniently an improved umami taste to food preparations without the use of additives and the inconvenience of yeasty aftertaste. The basic idea sustaining the present invention is to provide a taste enhancing savoury base that can be in any shelf stable and/or concentrated form and that may be used for seasoning meals and any type of savoury meals.

The present invention concerns a taste enhancing savoury base comprising:
 between 8 to 80% of naturally derived compounds taken in the group consisting of glutamate, IMP and GMP,
 naturally food derived compounds such as organic acids or their salts, amino acids, peptides and aroma compounds,
wherein said base is obtained through a bacterial fermentation with a bacteria taken in the group consisting of *Corynebacterium glutamicum, Corynebacterium ammoniagenes, Brevibacterium glutamicum, Brevibacterium ammoniagenes, Corynebacterium casei, Brevibacterium lactofermentum, Corynebacterium efficiens* and *Bacillus subtilis*
wherein the bacteria used for fermentation can or can not be removed from the fermentation broth
and wherein said base is not purified.

Furthermore, the bacteria used for fermentation can or can not be removed from the fermentation broth.

According to the invention, all the above mentioned components (glutamate, IMP, GMP, the naturally food derived compounds) are of natural origin because of the raw products used in the process. In the present specification, we define naturally derived glutamate, IMP and GMP, as compounds obtained via at least one of the following ways:
 extraction from raw material such as plant, animal,
 fermentation without purification during down stream processing or
 biocatalysis.

In the present specification, without purifications means that neither any compound of the fermentation broth has been crystallised nor any chemicals have been used for purification before drying nor any chromatographic separation technique has been carried out. The removal of cells is not to be understood as a purification.

Under glutamate, we understand glutamate anions in combination with any type of cations and/or free glutamic acid. Preferably, these cations are sodium or potassium cations. Under aroma compounds, we understand volatile compounds, like for example trimethylpyrazine, acetic acid or propionic acid.

All the percentages given are in weight, based on the dry matter.

According to an embodiment of the invention, the base contains between 8 and 80% of naturally derived compounds taken in the group consisting of glutamate, IMP and GMP. More specifically the base contains between 5 to 70% of naturally derived IMP and/or GMP and between 7 and 70% of glutamate.

It is possible according to the invention to produce a savoury base with only glutamate, or IMP and/or GMP or any combination. By only we understand that small levels of up to 2% of either IMP and/or GMP or glutamate can be present in the bases, respectively. In the first case, the amount of glutamate is comprised between 5 and 70%. Preferably, the amount of glutamate is comprised between 10 and 65%, most preferably between 30 and 65%. In the second case, the content of IMP and/or GMP is comprised between 15 and 70%, preferably between 30 and 50%. When glutamate, IMP and/or GMP are present, the total amount varies between 8 and 80%, preferably between 20 and 60%, most preferably between 30 and 50%.

The taste enhancing cultured savoury base comprises further
 sugars and
 macromolecules.

Under macromolecules, we understand polysaccharides, proteins and fats.

The type of sugars used according to the present invention is not critical. These sugars are of any type known in the art.

According to an embodiment of the invention, the quantity of natural glutamate, IMP and/or GMP is comprised between 10 and 80%. Preferably, this quantity is comprised between 10 and 60%.

An important feature of the invention is that the savoury base is produced in a natural way. The taste active components of the savoury base like glutamic acid, IMP and GMP are of natural origin, as they are not purified from the fermentation broth during downstream processing. As purification we consider crystallisation and chromatographic methods like ion exchange chromatography, hydrophobic interaction chromatography, size exclusion chromatography, affinity chromatography, adsorption chromatography etc. For determining the natural origin of these different components of the composition different techniques can be employed.

Trace amounts of RNA or DNA fragments of the prokaryote used during the fermentation process can be present in the final savoury base. These molecules can be isolated by amplification using PCR technique, which allows identifying the type of microorganism used for fermentation. In contrary, the presence of RNA or DNA molecules after subjecting the fermentation broth to purification techniques like crystallisation or chromatographic separation is very unlikely.

A second technique to proof the natural origin of taste active components is the identification of peptides and/or proteins present in the savoury base, originating from the microorganism used for fermentation. Identification can be done by mass spectrometry techniques like LC-MS/MS or MALDI-TOF/TOF. Comparison with protein databases allows concluding on the type of organism used for fermentation. Purification techniques like crystallisation however, will lead to separation of peptides and proteins from taste active molecules like glutamic acid or IMP and GMP.

The savoury base as such is very complex in its composition. It contains beside glutamate and/or IMP and/or GMP other compounds like organic acids, salts, amino acids, peptides, polysaccharides. This compounds would be lost during a purification process by crystallization as well as during chromatographic purification.

The savoury base provides improved umami sensory characteristics delivered in a natural way.

All the percentages in the present specification are given in weight.

The organic acids are mainly lactic acid, citric acid, acetic acid and malic acid. The amount of lactate is comprised between 0.01 and 8%, that of acetate between 0.01 and 6% and that of citrate between 0.01 and 8%.

The amino acids are mainly alanine, aspartic acid, glutamine, glutamic acid, glycine, leucine, lysine, methionine, tryptophan or valine.

The peptides are dipeptides, tripeptides or polypeptides.

Furthermore, the glutamate is not an added MSG, but natural glutamate, present on the base of the way of obtaining the cooking aid. The amount of glutamate is comprised between 0.01 and 70%. The amount of IMP and/or GMP is comprised between 0.01 and 70%.

NaCl is also present in the cooking aid according to the invention. The salt can be present naturally or can be also added, depending on the type of process and on the version concerned. The amount of salt can vary broadly.

The cooking aid further comprises between 0 and 20% of polysaccharides. These polysaccharides are taken from the group comprising derived cellulose, pectin, locust bean gum, starch, alone or in combination.

The shelf-stable cooking aid comprises further 0 to 70% of proteins. These protein are taken in the group comprising collagen, gelatine, myosin, actin, milk proteins, plant proteins, meat or fish proteins, alone or in combination. Further types of proteins are also possible.

Finally, the taste enhancing savoury base contains further at least one carbohydrate selected from the group comprising glucose, fructose, rhamnose, mannose, trehalose, sorbitol, glycerol, maltodextrines alone or in combination. Further carbohydrates are also possible.

Another feature of the invention is the low amount of fat, which is comprised between 0 and 15%. More particularly, the cooking aid has a free fatty acid content comprised between 0 and 3.2%.

Different forms of presentation can be considered for the product according to the invention. It is possible to have the composition in any physical form, like cube, powder, paste, concentrate, granule or liquid.

The present invention concerns further the use of a taste enhancing savoury base as described above, wherein the base is comprised in food products taken from the group consisting of
culinary products, such as bouillons, sauces, dehydrated soups,
dry foods including snacks, cereals and biscuits,
chilled and frozen products, like prepared meals,
nutritional products,
products for foodservice,
flavours and flavour ingredients
oral supplements,
pet foods,
beverages and
any other products where glutamate is part of the composition.

The amount of this savoury base is comprised between 0.01 and 50% based on the total weight of said product.

The typical umami organoleptic descriptors for deliciousness according to trained panel have been identified and listed as follows:
Fast Diffusion: corresponds to the first feeling that the consumer feels all over the mouth,
Full Body: corresponds to well-balanced, appropriate levels of all flavour notes that result in a favourable, complete, mouth feeling sensation,
Smoothness: corresponds to a smooth coating on the tongue,
Salivation: this corresponds to the intensity of salivation that the product generates just after consumption,
Retention: this is the post-consumption feeling that the product leaves in the mouth.

These five descriptors have been identified and are used to characterize and to hierarchise the different products made with the different ingredients used in different concentration.

It is noticeable that many descriptors refer to organoleptic features that are in relation not only with taste but are related to a textural effect. For example retention refers to a possible long interaction of the components of the stocks with the mouth mucus and epithelium on the tongue, where taste buds are located. So, one can notice that the deliciousness in the sense it is understood in the context of the present invention refers to a sensitive feeling that goes beyond the taste itself. The deliciousness may then be qualified as an interaction of taste with an occupation of the interior of the mouth thanks to an important or at least non-negligible textural effect.

There are different ways to use the cooking aid according to the invention. In the case of cubes, a paste or a powder, it is possible to add the cooking aid on the meal or in the meal, in a quantity depending on the taste wanted by the consumer. Normally, the cooking aid is added or mixed with the meal in a quantity of from 0.01 to 10% based on the total weight of the meal.

According to another feature, the invention concerns a method for bringing and/or enhancing taste in a meal by addition of a natural savoury base according to the invention in said meal in a quantity of from 0.01 to 50% based on the total weight of the meal.

According to a further feature, the invention concerns a process for the preparation of a taste enhancing savoury base as described before, comprising one or more of the processing steps described below:
Fermentation on substrate using a strain of *Corynebacterium glutamicum, Corynebacterium ammoniagenes, Corynebacterium casei, Brevibacterium lactofermentum, Corynebacterium efficiens* and *Bacillus subtilis*, cell disruption which yields a crude extract including cell debris.

According to an embodiment of the process of the invention, removal of cells or cell debris by filtration and/or centrifugation can be carried out, which yields a cell free broth. It is also possible to mix the broth with a natural hydrolysate in a ratio ranging from 0 to 99%.

The fermentation is carried out for obtaining the required amount of glutamate, which is then mixed with the product obtained according to the process object of the U.S. Pat. No. 6,838,100 as mentioned in the beginning of the specification: that means a product obtained by hydrolysing a protein-containing material using a combination of at least one enzyme with at least one thermotolerant lactic acid bacteria strain selected for its ability to provide a glutaminase activity. In this process, the enzyme is an exo- or endo-protease, deaminase, carbohydrase or amyloglucosidase.

According to this way of proceeding, the fermentation is carried out in 20 hours to 72 hours, at a pH comprised between 5 and 9 and at a temperature comprised between 25 and 40° C.

According to another feature of the invention, the process is more directed to increase the IMP and GMP content. In this case, the process is the same as above, but with other parameters concerning the reaction procedure.

As before, the natural hydrolysate is the product obtained according to U.S. Pat. No. 6,838,100.

In the case to increase the IMP and GMP content, the fermentation is carried out in 3 to 9 days, at a pH comprised between 5 and 9 and at a temperature comprised between 25 and 40° C.

It is clear that by proceeding according to the process to obtain more glutamate, there is also a presence of nucleotides and vice versa for the process increasing the nucleotides content.

In both of the above mentioned processes, it is also possible prior to mix with the natural hydrolysate to spray or vacuum/belt-dry the broth and convert it into any physical form, like powder, paste, cubes.

The substrate is preferably a natural substrate. This natural substrate used is from a carbon or nitrogen source of any kind, provided that they are utilizable for the strain employed. As for the carbon source, monosaccharides or oligosaccharides, like glucose, fructose, mannose, trehalose, sucrose, maltose, enzymatic hydrolysate of starch, molasses may be used separately or in combination of two or more. As for the nitrogen source, ammonia, urea, ammonium salts, like ammonium sulphate, amino acids, peptides, proteins, yeast extract, corn steep liquor, enzymatic hydrolysate of plant material or starch, meat or fish products may be used separately or in combination of two or more. Nutrients can be also added: these nutrients are for example phosphates, minerals or vitamins.

The plant material is taken from the group comprising wheat, corn, tapioca and rye.

The enzymatically treated starch is the starch of one of the above mentioned plants.

Finally, the present invention concerns a culinary food product containing between 0.01 and 50% of the taste enhancing base as described above.

Under food products, we understand
culinary products, such as bouillons, sauces, dehydrated soups,
dry foods including snacks, cereals and biscuits,
chilled and frozen products, like prepared meals,
nutritional products,
products for foodservice,
flavours and flavour ingredients
oral supplements,
pet foods,
beverages and
any other products where glutamate is part of the composition.

The following examples illustrate the invention in more details.

EXAMPLE 1

Glutamate

Enzymatically derived glucose is mixed with further substrates necessary for the growth of a microorganism. This mixture is inoculated with a fairly high cell concentration of a microorganism belonging to the genus of *Corynebacterium glutamicum*.

The fermentation is run during 24 hours, at a pH comprised between 6 and 7 and at a temperature of 40° C. During the fermentation with these parameters acids are excreted as a natural byproduct of the fermentation process.

The cells are inactivated via heat treatment and then separated by physical means from the fermentation medium, the naturally derived acids stay in the broth. The cells are removed by separation and the obtained filtrate is concentrated and spray-dried.

The obtained powder has a MSG content of 11%, a lactate content of 0.90%, an acetate content of 0.20% and a citrate content of 9.0%.

EXAMPLE 2

Ribonucleotides

A substrate is prepared as in example 1 and the fermentation is initiated with an inoculation according to example 1 With *Corynebacterium ammoniagenes*. The fermentation is run during 6 days, at a pH comprised between 6 and 8 and at a temperature of 30° C. During the fermentation with these parameters nucleotides such as IMP and/or GMP are excreted as a natural byproduct of the fermentation process.

The fermentation broth is further processed in the same manner as in example 1.

The obtained powder has a MSG content of 0.5%, an IMP content of 6.2%, a GMP content of 0.3% and an acetate content of 3.70%.

EXAMPLE 3

The products with naturally derived components obtained in example 1 and 2 are mixed together before and/or after the drying process. The products from example 1 and example 2 are mixed with a natural hydrolysate in order to obtain the best ratio for intense umami taste without off flavour for certain applications, e.g. in soups.

The natural hydrolysate serves as base and is added in an amount of up to 50%. This hydrolysate is mixed with 25% of product from example 1 and 25% of product from example 2. The mixed product is applied in culinary products in an amount depending on the type of application. For example, in the case of soup, the above mentioned product is added in an amount of around 2% and in the case of sauces, it is added in the amount of around 20%. The umami taste resulting from the application of the above described product is more intense than applying any commercially available and artificial taste enhancers.

EXAMPLE 4

The products according to example 1 and example 2 are mixed together before and/or after the drying process. The mixed powder is applied for a GC-MS analysis to determine the flavour active compounds. Therefore a Solid-Phase-microextraction (SPME) was used, and a sample of the headspace is injected.

The following compounds are present:
Trimethylpyrazine, Acetic acid, Propionic acid.

EXAMPLE 5

A sensory evaluation in culinary product application of a mixture of the powders described in Examples 1 and 2 resulted in the following outcome: the umami intensity is higher than the usage of the same weight amount of pure MSG.

The invention claimed is:

1. A process for the preparation of a taste enhancing savoury base comprising:
performing a fermentation on substrate using a microorganism of a species selected from the group consisting of *Corynebacterium glutamicum, Corynebacterium ammoniagenes, Brevibacterium lactofermentum, Corynebacterium casei, Corynebacterium efficiens* and *Bacillus subtilis*; and
using naturally food derived compounds and between 8 to 80% naturally derived compounds obtained by the fermentation selected from the group consisting of glutamate, inosine monophosphate (IMP) and guanosine monophosphate (GMP) to produce a base;
wherein the base is not purified by crystallization or chromatographic methods.

2. The process according to claim 1, comprising
performing a cell disruption on cells of the microorganism contained in broth from the fermentation to yield a crude extract including cell debris; and
removal of cells or cell debris from the crude extract by filtration and/or centrifugation to obtain the naturally derived compounds from the fermentation.

3. The process according to claim 1, comprising mixing the broth with natural hydrolysate.

4. The process according to claim 1, wherein the fermentation is performed in 20 to 72 hours, at a pH between 5 and 9 and at a temperature between 25 and 40° C.

5. The process according to claim 1, wherein the fermentation is performed in 3 to 6 days, at a pH between 5 and 9 and at a temperature between 25 and 40° C.

6. The process according to claim 3, wherein prior to mixing with the natural hydrolysate the broth is dried and converted into a physical form.

7. The process according to claim 1, wherein the substrate is selected from the group consisting of a carbon and nitrogen source.

8. The process according to claim 1, wherein the substrate is obtained by the enzymatic hydrolysis of a plant material or by the enzymatic hydrolysis of starch.

9. The process according to claim 8, wherein the plant is selected from the group consisting of wheat, corn, tapioca, and rye.

* * * * *